United States Patent
Kayton et al.

(10) Patent No.: US 12,076,155 B2
(45) Date of Patent: Sep. 3, 2024

(54) SYSTEMS AND METHODS FOR MONITORING PHYSIOLOGICAL PARAMETERS DURING DIATHERMY

(71) Applicant: MEDASENSE BIOMETRICS LTD., Ramat Gan (IL)

(72) Inventors: Avi Kayton, Tel Aviv (IL); Aviem Amossi, Tel Aviv (IL); Shauli Arazi, Tel Aviv (IL)

(73) Assignee: MEDASENSE BIOMETRICS LTD., Ramat Gan (IL)

( * ) Notice: Subject to any disclaimer, the term of this patent is extended or adjusted under 35 U.S.C. 154(b) by 899 days.

(21) Appl. No.: 17/261,146

(22) PCT Filed: Jul. 21, 2019

(86) PCT No.: PCT/IL2019/050815
§ 371 (c)(1),
(2) Date: Jan. 18, 2021

(87) PCT Pub. No.: WO2020/021531
PCT Pub. Date: Jan. 30, 2020

(65) Prior Publication Data
US 2021/0315633 A1 Oct. 14, 2021

Related U.S. Application Data

(60) Provisional application No. 62/701,825, filed on Jul. 22, 2018.

(51) Int. Cl.
*A61B 5/00* (2006.01)
*A61B 5/024* (2006.01)
(Continued)

(52) U.S. Cl.
CPC ........ *A61B 5/4035* (2013.01); *A61B 5/02416* (2013.01); *A61B 5/0531* (2013.01);
(Continued)

(58) Field of Classification Search
CPC . A61B 5/4035; A61B 5/02416; A61B 5/0531; A61B 5/7217; A61B 5/7225; A61B 5/725
See application file for complete search history.

(56) References Cited

U.S. PATENT DOCUMENTS

| 8,536,391 B2 | 9/2013 | Small et al. |
| 2013/0030267 A1 | 1/2013 | Lisogurski et al. |
| 2018/0279953 A1* | 10/2018 | Wang ............... A61B 5/318 |

FOREIGN PATENT DOCUMENTS

| JP | H09-308638 | 12/1997 |
| JP | 2012-516205 | 7/2012 |

(Continued)

OTHER PUBLICATIONS

PCT Search Report for International Application No. PCT/IL2019/050815 mailed Nov. 5, 2019, 3 pp.

(Continued)

*Primary Examiner* — Tammie K Marlen
(74) *Attorney, Agent, or Firm* — Greenberg Traurig, LLP

(57) ABSTRACT

Disclosed is a system for monitoring physiological parameters during a medical interventional procedure involving high intensity/energy radiofrequency electrical currents/voltages applied through a body of a subject, the system including an electrode-based sensor, configured to close an electrical conduction path passing through a body of a subject, and one or more non-electrode-based sensors, a plurality of electrical lines, a monitor, and a filter array including EMI filters mounted at specific locations and characterized by a frequency response curve having a magnitude of an attenuation in a first frequency range (typical of operating frequencies of high intensity/energy radiofrequency medical interventional equipment), which is greater than a magnitude of an attenuation in a second frequency range (typical of the sampling frequencies of the electrode-based sensor and the one or more non-electrode-based (Continued)

sensors), the system being thereby configured for suppressing noise induced by the medical interventional equipment.

9 Claims, 2 Drawing Sheets

(51) Int. Cl.
    *A61B 5/0531*     (2021.01)
    *A61B 18/14*     (2006.01)
    *A61B 18/00*     (2006.01)

(52) U.S. Cl.
    CPC .......... *A61B 5/4824* (2013.01); *A61B 5/7217* (2013.01); *A61B 5/7225* (2013.01); *A61B 5/725* (2013.01); *A61B 18/14* (2013.01); *A61B 2018/00577* (2013.01); *A61B 2018/00773* (2013.01)

(56) References Cited

FOREIGN PATENT DOCUMENTS

| | | |
|---|---|---|
| JP | 2012-530185 A | 11/2012 |
| WO | 2010090835 A1 | 8/2010 |

OTHER PUBLICATIONS

PCT Written Opinion for International Application No. PCT/IL2019/050815 mailed Nov. 5, 2019, 5 pp.

PCT Preliminary Report on Patentability for International Application No. PCT/IL2019/050815 dated Jan. 26, 2021, 6 pp.

\* cited by examiner

SYSTEMS AND METHODS FOR MONITORING PHYSIOLOGICAL PARAMETERS DURING DIATHERMY

CROSS REFERENCE TO RELATED APPLICATIONS

This application is a National Phase of PCT Patent Application No. PCT/IL2019/050815 having International filing date of Jul. 21, 2019, which claims the benefit of priority of U.S. Provisional Patent Application No. 62/701,825, filed Jul. 22, 2018, the contents of which are all incorporated herein by reference in their entirety.

TECHNICAL FIELD

The present disclosure relates generally to multi-parameter physiological signal acquisition during a medical procedure, including application of radiofrequency alternating polarity electrical currents through a body of a patient.

BACKGROUND

In a diathermy surgical procedure (also referred to herein as electrosurgery or electrocautery), an electrical current is applied through electrodes such as to close an electrical conduction path passing through the body of a patient. The electrical current is applied at radiofrequency such as to heat tissue at a target site on the body of the patient, thereby cutting, desiccating, and/or fulgurating the tissue, while simultaneously coagulating the tissue and reducing blood loss. The device applying the current may contact the skin of the patient or may be held proximately thereto when a high enough voltage is applied to generate an electrical arc.

The electrical current/energy produced in a diathermy procedure may affect medical sensors contacting the body of the patient, adding noise to the signals produced by the sensors, with a resultant signal deformation or even signal saturation (i.e. complete loss of the signal). In particular, diathermy/electrocautery induced-noise may affect electrode-based sensors (e.g. ECG, EMG, or a galvanic skin response sensor). Due to the high energies (high currents and/or high voltages) involved, electrical interference effects (e.g. capacitive coupling, inductive coupling) may also deform/saturate signals of medical/physiological sensors which do not contact the body, but which are positioned proximately (closely) to an "affected" medical sensor, such as an electrode-based sensor.

In particular, diathermy-induced noise is detrimental to reliable monitoring of parameters (during diathermy/electrosurgery), and, as such, is detrimental to reliable assessment of e.g. the patient's physiological status and the patient's pain or nociception level during diathermy. The lack of ability to reliably monitor pain or nociception during a diathermy surgical procedure may result in patients receiving excessive or insufficient dosages of anesthetics. Excessive dosages of anesthetics may contribute to hypotension and myocardial injuries and/or acute kidney injuries which may appear even months after surgery, as well as hyperalgesia. Insufficient dosages of anesthetics may on the other hand lead to a severe stress response that may be dangerous to a frail patient and may lead (post-surgery) to persistent and/or chronic pain.

There thus remains a need for reliable systems and methods for pain monitoring during a diathermy procedure.

SUMMARY

Aspects of the disclosure, according to some embodiments thereof, relate to monitoring of one or more physiological parameters during procedures involving application of high intensity/energy radiofrequency electrical currents/voltages through a body of a patient, such as, but not limited to, diathermy, RF ablation, etc. Specifically, some aspects of the disclosure relate to reliably assessing a patient's autonomic nervous system activity, during a diathermy or electrocautery procedure, by monitoring one or more physiological parameters. More specifically, but not exclusively, aspects of the disclosure, according to some embodiments thereof, relate to suppression of diathermy-induced noise in physiological sensors, such as noise induced in non-electrode-based sensors due to the proximity thereof to an electrode-based sensor.

The present disclosure advantageously provides reliable monitoring of pain, nociception, anesthesia, stress, anxiety, sleep, and/or analgesia during a diathermy surgical procedure by means of electromagnetic interference (EMI) filters placed at specific locations between the medical sensors used to obtain physiological data from a patient and the monitor used to process the sensor data to assess the level/degree of pain, nociception, anesthesia, stress, anxiety, sleep, and/or analgesia of the patient. More generally, the present disclosure provides reliable monitoring of a plurality of physiological parameters and autonomic nervous system activity of patients undergoing a diathermy surgical procedure.

Thus, according to an aspect of some embodiments, there is provided a system including a sensor assembly, a monitor, a plurality of electrical lines, and a filter array. The sensor assembly includes at least one electrode-based sensor configured to close an electrical conduction path passing through a body of a subject, and one or more non-electrode-based sensors configured to monitor one or more physiological parameters of the subject during a medical interventional procedure involving an application of at least one chosen from: (i) high intensity radiofrequency electrical currents, (ii) high intensity radiofrequency electrical voltages, (iii) high energy radiofrequency electrical currents, and (iv) high energy radiofrequency electrical voltages. The plurality of electrical lines electrically associates the sensor assembly with the monitor. The plurality of electrical lines includes a first line configured to transmit a plurality of first sensor signals from the electrode-based sensor to the monitor, and a second line configured to transmit a plurality of second sensor signals from the one or more non-electrode-based sensors to the monitor. The monitor is configured to assess physiological activity of the subject based at least on the plurality of second sensor signals. The filter array includes a first proximal electromagnetic interference (EMI) filter mounted on the first line, a second distal EMI filter mounted on the first line, and a third EMI filter mounted on the second line. The first proximal EMI filter is positioned between the electrode-based sensor and the second distal EMI filter. Each of the second distal EMI filter and the third EMI filter is characterized by a respective frequency response curve with a magnitude of an attenuation in a first frequency range greater by at least 10 dB than the magnitude of the attenuation in a second frequency range. A combination of the sensor assembly, the plurality of electrical lines and the filter array is configured to suppress noise induced by medical interventional equipment used in the medical interventional procedure.

According to some embodiments, the first proximal EMI filter is mounted on the first line in or near the sensor assembly.

According to some embodiments, the second distal EMI filter is mounted on the first line in or near the monitor.

According to some embodiments, the first frequency range is typical of operating frequencies of high intensity and/or high energy radiofrequency medical interventional equipment.

According to some embodiments, the second frequency range is typical of sampling frequency/frequencies of the electrode-based sensor and the one or more non-electrode-based sensors.

According to some embodiments, the magnitude of the attenuation of the second and the third EMI filters in the first frequency range is at least about 60 dB.

According to some embodiments, the magnitude of the attenuation of the first EMI filter in the first frequency range is at least about 10 dB, and/or the magnitude of the attenuation of the first EMI filter in the first frequency range is greater by at least about 10 dB than the magnitude of the attenuation thereof in the second frequency range.

According to some embodiments, the first frequency range is between about 300 kHz and about 500 kHz.

According to some embodiments, the second frequency range is between 0 Hz to about 600 Hz.

According to some embodiments, the sensor assembly is a finger probe configured to be mounted on a finger of the subject.

According to some embodiments, the electrode-based sensor includes a bio-impedance sensor and/or a bio-potential sensor.

According to some embodiments, the electrode-based sensor includes a galvanic skin response (GSR) sensor, an electrocardiograph (ECG), an electromyograph (EMG), an electrogastrograph (EGG), an electroencephalograph (EEG), and/or an electrooculograph (EOG).

According to some embodiments, the electrode-based sensor is a GSR sensor.

According to some embodiments, the monitor includes an analog-to-digital converter (ADC). The distal filter is mounted at or near an input terminal of the ADC.

According to some embodiments, the first line extends from the electrode-based sensor to the ADC. An input terminal of the proximal filter is coupled to the electrode-based sensor. An output terminal of the proximal filter is configured to transmit, via the first line, a filtered electrode-based sensor signal. A ground terminal of the proximal filter is connected to a floating ground. An input terminal of the distal filter is configured to receive, via the first line, the filtered electrode-based sensor signal. An output terminal of the distal filter is coupled to the ADC. A ground terminal of the distal filter is connected to the floating ground.

According to some embodiments, the system further includes an amplifier mounted on the first line in between the proximal filter and distal filter and configured to amplify the filtered electrode-based sensor signal.

According to some embodiments, the non-electrode-based sensor includes a photoplethysmogram (PPG) sensor, a piezo-electric sensor, an accelerometer, a thermometer, a blood pressure sensor, a respiration sensor, a near infrared spectroscopy (NIRS) sensor, a dynamical light scattering (DLS) based sensor, a laser doppler flowmeter, a diffused correlation spectroscopy (DCS) based sensor, an acoustic sensor, and/or a microphone.

According to some embodiments, the non-electrode-based sensor is a PPG sensor.

According to some embodiments, the sensor assembly further includes a third sensor, which is non-electrode-based. The plurality of electrical lines further includes at least one additional line configured to transmit a sensor signal(s) from the third sensor to the monitor. The filter array further includes at least one additional EMI filter mounted on the at least one additional line.

According to some embodiments, the third sensor is an accelerometer. The at least one additional line includes at least three lines. The at least one additional EMI filter includes at least three EMI filters mounted on the at least three lines, respectively.

According to some embodiments, wherein the non-electrode-based sensor is a PPG sensor, the third filter is mounted at, or near, a second input terminal of the ADC or at, or near, the input terminal of a second ADC in the monitor.

According to some embodiments, an input terminal of the third filter is configured to receive, via the second line, a second sensor signal from the non-electrode-based sensor. An output terminal of the third filter is coupled to the ADC. A ground terminal of the third filter is connected to the floating ground.

According to some embodiments, the system further includes a second amplifier mounted on the second line before the third filter and configured to amplify the sensor signal received from the non-electrode-based sensor.

According to some embodiments, the proximal EMI filter is housed within the sensor assembly and all the other EMI filters in the filter array are housed within the monitor.

According to some embodiments, wherein the system includes the amplifier and the second amplifier, the amplifiers are housed within the monitor.

According to some embodiments, in between the sensor assembly and the monitor, the plurality of electrical lines is housed within an electrical cable.

According to some embodiments, the electrical cable is about 2.8 m long.

According to some embodiments, the monitor includes a processor configured to allow assessing, based on the sensor signals, a physiological status of the subject during the medical interventional procedure.

According to some embodiments, the assessing of the physiological status during the medical interventional procedure includes discounting (not taking into account, ignoring) data received from the electrode-based sensor.

According to some embodiments, the physiological status is an autonomic nervous system activity of the subject.

According to some embodiments, the autonomic nervous system activity includes one or more of a level of pain, nociception, anesthesia, analgesia, anxiety, and/or stress of the subject.

According to some embodiments, the autonomic nervous system activity is a level of pain of the subject.

According to some embodiments, each of the at least three EMI filters is a low ESL (equivalent series inductance) feed-through capacitor.

According to some embodiments, a capacitance of the first EMI filter is between about 0.05 µF and 0.2 µF.

According to some embodiments, capacitances of the second and the third EMI filters are between about 15 µF and about 40 µF.

According to some embodiments, the sensor assembly further includes a thermometer, and the plurality of electrical lines includes a thermometer-dedicated line configured to transmit sensor data obtained by the thermometer to the monitor.

According to some embodiments, the medical interventional procedure is diathermy.

According to some embodiments, the medical interventional procedure is RF ablation.

According to some embodiments, the proximal EMI filter is mounted near or adjacently to the first sensor.

According to some embodiments, the assessing of the physiological status during the medical interventional procedure includes cleaning the signals obtained from the at least one non-electrode-based sensor on an estimation of noise introduced through the at least one electrode-based sensor.

According to an aspect of some embodiments, there is provided a system including:

- At least one electrode-based sensor configured to close an electrical conduction path passing through a body of a subject.
- At least one non-electrode-based sensor configured to monitor one or more physiological parameters of the subject during a medical interventional procedure involving an application of at least one chosen from high intensity radiofrequency electrical currents, high intensity radiofrequency electrical voltages, high energy radiofrequency electrical currents, and high energy radiofrequency electrical voltages.
- an analog-to-digital converter.
- A control circuitry.
- An electromagnetic interference (EMI) filter.

The EMI filter is configured to receive a plurality of first sensor signals from the at least one electrode-based sensor, to filter the first sensor signals, and to transmit the filtered first sensor signals to the analog-to-digital converter. The non-electrode-based sensor is configured to transmit a plurality of second senor signals to the analog-to-digital converter and/or to the control circuitry. The analog-to-digital converter is configured to convert the filtered first sensor signals, and optionally the second sensor signals, into digital signals, and to transmit the digital signals to the control circuitry. The EMI filter is configured to suppress noise in the signal of the at least one electrode-based sensor induced by medical interventional equipment used in the medical interventional procedure.

According to some embodiments, the system further includes a first line and a second line. The EMI filter is mounted on the first line. The plurality of first sensor signals are relayed from the at least one electrode-based sensor to the analog-to-digital converter via the first line (and filtered on the way by the EMI filter). The plurality of second sensor signals are relayed from the at least one non-electrode-based sensor to the analog-to-digital converter, and/or to the control circuitry, via the second line.

According to some embodiments, the system further includes a wireless communication unit.

According to some embodiments, the wireless communication unit is configured to receive signals from the control circuitry and wirelessly transmit the signals to an external monitor configured to process the signals and to assess a physiological status of the subject based thereon.

According to some embodiments, the control circuitry includes a processor circuitry configured to process the digital signals obtained from the analog-to-digital converter and to assess the physiological status of the subject based thereon.

According to some embodiments, the processing of the signals includes cleaning the signals obtained from the at least one non-electrode-based sensor on an estimation of noise introduced through the at least one electrode-based sensor.

According to some embodiments, the assessing of the physiological status during the medical interventional procedure includes discounting data received from the electrode-based sensor.

According to some embodiments, an attenuation of the EMI filter in a first frequency range is at least about 10 dB, and/or the magnitude of the attenuation of the EMI filter in the first frequency range is greater by at least about 10 dB than the magnitude of the attenuation thereof in a second frequency range.

According to some embodiments, the first frequency range is typical of operating frequencies of high intensity and/or high energy radiofrequency medical interventional equipment and the second frequency range is typical of sampling frequency/frequencies of the electrode-based sensor and the at least one non-electrode-based sensor.

According to some embodiments, the first frequency range is between about 300 kHz and about 500 kHz and the second frequency range is between 0 Hz to about 600 Hz.

According to some embodiments, the sensor assembly is a finger probe configured to be mounted on a finger of the subject.

According to some embodiments, the at least one electrode-based sensor includes a bio-impedance sensor and/or a bio-potential sensor.

According to some embodiments, the at least one electrode-based sensor includes a galvanic skin response (GSR) sensor, an electrocardiograph (ECG), an electromyograph (EMG), an electrogastrograph (EGG), an electroencephalograph (EEG), and/or an electrooculograph (EOG).

According to some embodiments, the electrode-based sensor is a GSR sensor.

According to an aspect of some embodiments, there is provided a system for monitoring physiological parameters during a medical interventional procedure involving high intensity/energy radiofrequency electrical currents/voltages applied through a body of a subject. The system includes a sensor assembly, a plurality of electrical lines, a monitor, and a filter array. The sensor assembly includes an electrode-based sensor, configured to close an electrical conduction path passing through a body of a subject, and one or more non-electrode-based sensors configured to monitor one or more physiological parameters of the subject. The plurality of electrical lines associates the sensor assembly with the monitor and includes a first line and a second line configured to transmit sensor signals from the electrode-based sensor and the one or more non-electrode-based sensors to the monitor. The monitor is configured to assess physiological activity of a subject based on at least some of the sensor signals. The filter array includes at least three electromagnetic interference (EMI) filters:

- a first, proximal filter mounted on the first line in or near the sensor assembly;
- a second, distal filter mounted on the first line in or near the monitor; and
- a third filter mounted on the second line.

At least some of the EMI filters are characterized by a frequency response curve such that a magnitude of an attenuation in a first frequency range, which is typical of operating frequencies of high intensity/energy radiofrequency medical interventional equipment, is greater by at least 10 dB than a magnitude of an attenuation in a second frequency range, which is typical of sampling frequency/frequencies of the electrode-based sensor and the one or more non-electrode-based sensors. The system is thereby configured for suppressing noise induced by the medical interventional equipment.

Certain embodiments of the present disclosure may include some, all, or none of the above advantages. One or more other technical advantages may be readily apparent to those skilled in the art from the figures, descriptions, and claims included herein.

Moreover, while specific advantages have been enumerated above, various embodiments may include all, some, or none of the enumerated advantages.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

Unless specifically stated otherwise, as apparent from the disclosure, it is appreciated that, according to some embodiments, terms such as "processing", "computing", "calculating", "determining", "estimating", "assessing", "gauging" or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present disclosure may include apparatuses for performing the operations herein. The apparatuses may be specially constructed for the desired purposes or may include a general purpose computer(s) selectively activated or reconfigured by a computer program stored in the computer. Such a computer program may be stored in a computer readable storage medium, such as, but not limited to, any type of disk including floppy disks, optical disks, CD-ROMs, magnetic-optical disks, read-only memories (ROMs), random access memories (RAMs), electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method(s). The desired structure(s) for a variety of these systems appear from the description below. In addition, embodiments of the present disclosure are not described with reference to any particular programming language. It will be appreciated that a variety of programming languages may be used to implement the teachings of the present disclosure as described herein.

Aspects of the disclosure may be described in the general context of computer-executable instructions, such as program modules, being executed by a computer. Generally, program modules include routines, programs, objects, components, data structures, and so forth, which perform particular tasks or implement particular abstract data types. Disclosed embodiments may also be practiced in distributed computing environments where tasks are performed by remote processing devices that are linked through a communications network. In a distributed computing environment, program modules may be located in both local and remote computer storage media including memory storage devices.

BRIEF DESCRIPTION OF THE FIGURES

Some embodiments of the disclosure are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the disclosure. For the sake of clarity, some objects depicted in the figures are not to scale.

In the Figures.

DETAILED DESCRIPTION

Figure 1:
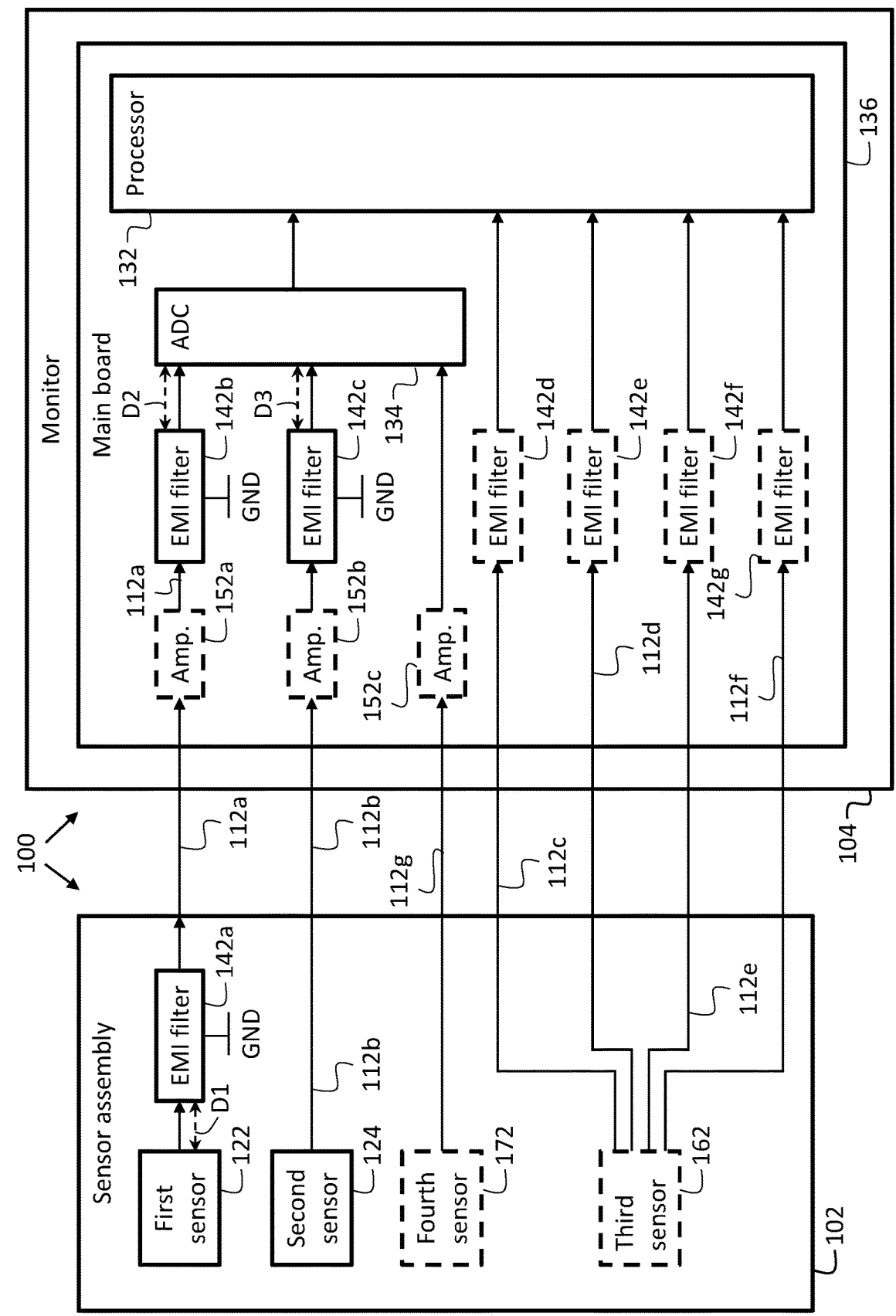
FIG. 1 is a block diagram of a system configured for monitoring physiological parameters during an interventional medical procedure, such as a diathermy surgical procedure, according to some embodiments.

The principles, uses, and implementations of the teachings herein may be better understood with reference to the accompanying description and figures. Upon perusal of the description and figures present herein, one skilled in the art will be able to implement the teachings herein without undue effort or experimentation. In the figures, same reference numerals refer to same parts throughout.

In the description and claims of the application, the words "include" and "have", and forms thereof, are not limited to members in a list with which the words may be associated.

As used herein, the term "about" may be used to specify a value of a quantity or parameter (e.g. the length of an element) to within a continuous range of values in the neighborhood of (and including) a given (stated) value. According to some embodiments, "about" may specify the value of a parameter to be between 80% and 120% of the given value. For example, the statement "the length of the element is equal to about 1 m" is equivalent to the statement "the length of the element is between 0.8 m and 1.2 m". According to some embodiments, "about" may specify the value of a parameter to be between 90% and 110% of the given value. According to some embodiments, "about" may specify the value of a parameter to be between 95% and 105% of the given value.

FIG. 1 is a block diagram of a monitoring system 100 including a plurality of physiological sensors, according to some embodiments. According to some embodiments, monitoring system 100 may be a multi-parameter physiological monitoring system configured to monitor multiple (e.g. at least 2, at least 3, or at least 4) physiological parameters of a subject. According to some embodiments, monitoring system 100 may be a vital signs monitoring system configured to monitor at least 2, at least 3, or at least 4 vital signs of a subject, e.g. pulse rate, temperature, respiration rate, blood pressure, and/or other parameters indicative of the state of a patient's essential body functions. According to some embodiments, monitoring system 100 may be an autonomic nervous system monitoring system configured to monitor at least 2, at least 3, or at least 4 parameters indicative of autonomic nervous system activity/function.

The plurality of physiological sensors includes an electrode-based sensor and at least one non-electrode-based sensor, as elaborated on below. Monitoring system 100 is configured to measure at least one physiological parameter of a subject undergoing a medical procedure in which high intensity/energy radiofrequency electrical currents/voltages are applied through the body of the subject such as, but not limited to, diathermy and RF ablation procedures, thereby, for example, allowing assessment of an autonomic nervous system activity of the subject (during the procedure). According to some embodiments, monitoring system 100 may be configured to assess the level of pain experienced by the subject (during the procedure), as elaborated on below. Additionally or alternatively, monitoring system 100 may be configured to monitor analgesia, nociception, anesthesia, stress, and/or anxiety of the subject during the procedure.

Monitoring system 100 includes a sensor assembly 102, a monitor 104, electrical lines 112, and a filter array (including a plurality of EMI filters as specified below). According to some embodiments, sensor assembly 102 may include an electrode-based sensor and at least one non-electrode-based sensor, positioned in proximity to one another, e.g. distanced from one another by less than 10 cm, less than 5 cm, less than 2 cm, less than 1 cm, or less than 0.5 cm. Each possibility is a separate embodiment. According to some embodiments, sensor assembly 102 is powered via monitor 104.

Sensor assembly 102 includes a first sensor 122 and a second (additional) sensor 124. First sensor 122 is an electrode-based sensor including electrodes (e.g. at least two electrodes) configured to close one or more electrical conduction paths passing through a body of a subject. First sensor 122 may be any bio-impedance sensor and/or bio-potential sensor. Non-limiting examples of suitable bio-impedance and/or bio-potential sensors include an electrocardiograph (ECG), an electromyograph (EMG), an electrogastrograph (EGG), an electroencephalograph (EEG), and/or an electrooculograph (EOG). Each possibility is a separate embodiment. According to some embodiments, first sensor 122 may be or include a galvanic skin response (GSR) sensor.

Second sensor 124 may be configured to monitor another physiological parameter of the subject. According to some embodiments, second sensor 124 is a non-electrode-based sensor, and the monitoring effected by second sensor 124 does not involve the closing of an electrical conduction path through the body of the subject. Non-limiting examples of suitable non-electrode-based sensors include a piezo-electric sensor, an accelerometer, a thermometer, a blood pressure sensor, a respiration sensor, a near infrared spectroscopy (NIRS) sensor (e.g. to quantify oxygen saturation), a dynamical light scattering (DLS) based sensor, a laser doppler flowmeter (e.g. to quantify blood flow), a diffused correlation spectroscopy (DCS) based sensor (e.g. to monitor blood flow), an acoustic sensor, and a microphone. Each possibility is a separate embodiment. According to some embodiments, second sensor 124 may include more than one sensor, e.g. 2, 3, 4, 5 or more sensors. Each possibility is a separate embodiment. As a non-limiting example, second sensor 122 may include two or more piezoelectric sensors such as to allow the extraction of pulse transit time (Ptt) readings. According to some embodiments, second sensor 122 may include a piezoelectric sensor and a PPG sensor such as to allow the extraction of Ptt readings. According to some embodiments, second sensor 122 may include two or more spaced-apart PPG sensors such as to allow the extraction of Ptt readings. According to some such embodiments, second sensor 122 may be configured to allow the extraction of a pulse speed wave for determining Ptt and blood pressure related parameters. According to some embodiments, second sensor 124 may be or include a photoplethysmogram (PPG) sensor.

According to some embodiments, first sensor 122 and second sensor 124 may each be configured to sample at a rate of between about 10 Hz and about 2 kHz or between about 50 Hz and about 1 kHz. According to some embodiments, first sensor 122 and second sensor 124 may each be configured to sample at a rate of about 500 Hz. According to some embodiments, sensor assembly 102 may be configured to be mounted/placed on the patient's body e.g. on a forehead, a back, a chest, a foot, an arm, a hand (e.g. on the back of the hand), and/or an ear (e.g. in the earlobe) of the patient. Each possibility is a separate embodiment. According to some embodiments, sensor assembly 102 may be a finger probe configured to be mounted/worn on a finger of the subject.

Electrical lines 112 electrically connect sensor assembly 102 and monitor 104. Electrical lines 112 are configured for transmission of sensor data obtained by first sensor 122 and second sensor 124 (and, optionally, when present, additional sensors) to monitor 104, as elaborated on below.

According to some embodiments, sensor assembly 102 includes control circuitry (including e.g. a micro-controller; not shown) functionally associated with first sensor 122 and second sensor 124 and configured to control first sensor 122 and second sensor 124 operation (and the operation of additional sensors in embodiments wherein sensor assembly 102 includes additional sensors).

Monitor 104 includes processing circuitry configured to process sensor data, received from sensor assembly 102, and to assess, based on the sensor data, the physiological status of the subject, e.g. the activity of the subject's autonomic nervous system, during high intensity/energy radiofrequency interventional procedures such as diathermy. According to some embodiments, the processing circuitry includes a at least one processor 132, a memory (not shown), and an analog-to-digital converter (ADC) 134 configured to convert analog sensor data into one or more digital signals, which are fed into processor 132. The processing circuitry may be mounted/positioned on a main board 136 (a printed circuit board). Monitor 104 may additionally include a user interface (including a display) and a wireless communication unit and/or a port for wired communication (all not shown).

Processor 132 may include one or more microprocessors, application-specific integrated circuits (ASICs), field-programmable gate arrays (FPGAs), firmware, and/or the like (all not shown). In particular, processor 132 may include one or more customized processors for analyzing sensor data such as to obtain therefrom physiological parameters of a subject and to assess, based thereon, an autonomic nervous system activity of the subject (e.g. a level of pain experienced by the subject).

The memory may include transitory memory components and/or non-transitory memory components, which may be solid-state, magnetic, photonic, and/or the like. According to some embodiments, some or all of the memory components may be integrated together or distributed. According to some embodiments, the memory may be wholly or partially integrated with processor 132. The memory has stored therein software instructions executable by processor 132 to analyze sensor data, as described above.

According to some embodiments, sensor assembly 102 and monitor 104 may be functionally associated such that sensor assembly 102 controllable functions (e.g. activating/ deactivating a sensor) can be controlled using monitor 104 (e.g. via the user interface thereof).

The filter array includes a plurality of EMI filters 142. According to some embodiments, EMI filters 142 may be characterized by a frequency response curve with a minimum (when the gain is plotted as a function of the frequency) in a frequency range corresponding to the operating frequencies of the noise-inducing medical device. According to some embodiments, at least some of EMI filters 142 may be characterized by a frequency response curve having a magnitude of attenuation in a first frequency range greater by at least 10 dB than a magnitude of attenuation in a second frequency range (that is, the gain in the first frequency range is lower by at least 10 dB than the gain in the second frequency range). The first frequency range may be typical of operating frequencies (applied current frequencies) of diathermy, RF ablation, and similar surgical equipment. The second frequency range may characterize the sampling frequency of the sensors. According to some embodiments, at least some of EMI filters 142 may be characterized by a frequency response curve with a minimum between 100 kHz and 5 MHz, for example, when the noise-inducing medical device is diathermy electrosurgical equipment. According to some embodiments, the minimum is a global minimum (maximum attenuation). According to some embodiments, at least some of EMI filters 142 may attenuate frequencies in the 300 kHz to 500 kHz range by at least about 50 dB, at least about 55 dB, at least about 60 dB, or at least about 70 dB (i.e. the gain is at least about −50 dB, −55 dB, −60 dB, or −70 dB, respectively). Each possibility is a separate embodiment.

According to some embodiments, a magnitude of the attenuation in the 300 kHz to 500 kHz range is at least about 10 dB, at least about 15 dB, at least about 20 dB greater, or at least about 50 dB greater than in the 0 Hz to 600 Hz range. Each possibility is a separate embodiment. The EMI filters are thus configured to suppress diathermy/RF ablation-induced noise and enable reliable measurement of physiological parameters (e.g. by second sensor 124).

According to some embodiments, a first (proximal) EMI filter 142a (from EMI filters 142) may be mounted on a first line 112a (from electrical lines 112) in or near sensor assembly 102 and may be configured to filter first sensor 122 measurement data. According to some embodiments, and as elaborated on below, first EMI filter 142a may be characterized by a capacitance of about 0.1 µF. According to some embodiments, the relatively low capacitance of first EMI filter 142a may help to preserve signals obtained from first sensor 122. According to some embodiments, first EMI filter 142a may attenuate frequencies in the 300 kHz to 500 kHz range by about 5 dB, about 10 dB, about 20 dB, or about 25 dB.

Additionally or alternatively, a second (distal) EMI filter 142b (from EMI filters 142) may be mounted on first line 112a in or near monitor 104. According to some embodiments, and as elaborated on below, second EMI filter 142b may be characterized by a capacitance of between about 20 µF and about 30 µF. According to some embodiments, the second EMI filter 142b may attenuate frequencies in the 300 kHz to 500 kHz range by about at least about 50 dB, at least about 55 dB, at least about 60 dB, or at least about 70 dB.

First EMI filter 142a and second EMI filter 142b may be serially mounted on first line 112a such that first sensor 122 measurement data undergoes filtering twice. Specifically, second EMI filter 142b may be configured to filter (already once filtered) measurement data received from first EMI filter 142a.

A third EMI filter 142c (from EMI filters 142) may be mounted on a second line 112b (from electrical lines 112). According to some embodiments, including some embodiments wherein second sensor 124 is a non-electrode-based sensor (e.g. a PPG sensor), third EMI filter 142c may be mounted on second line 112b in or near monitor 104. According to some embodiments, and as elaborated on below, third EMI filter 142c may be characterized by a capacitance of between about 20 µF and about 30 µF. According to some embodiments, the third EMI filter 142c may attenuate frequencies in the 300 kHz to 500 kHz range by about at least about 50 dB, at least about 55 dB, at least about 60 dB, or at least about 70 dB.

The positioning of EMI filters 142a-142c may lead to reliable diathermy-induced noise suppression. In particular, the positioning of first EMI filter 142a at the beginning (proximal end) of first line 112a helps reduce EMI interference between first line 112a and second line 112b (e.g. due to capacitive coupling between the two lines along the lengths thereof).

According to some embodiments, an input terminal of first EMI filter 142a may be electrically coupled to first sensor 122 and may be configured to receive therefrom measurement data of first sensor 122. According to some embodiments, first EMI filter 142a may be positioned such that the input terminal thereof is adjacent to first sensor 122. An output terminal of first EMI filter 142a may be configured to relay first sensor 122 filtered measurement data to monitor 104 via first line 112a. A ground terminal of first EMI filter 142a may be connected to a first floating ground (e.g. a signal ground).

According to some embodiments, an input terminal of second EMI filter 142b may be configured to receive filtered first sensor 122 measurement data via first line 112a. An output terminal of first EMI filter 142a may be electrically coupled to ADC 134 and may be configured to relay twice-filtered first sensor 122 measurement data to ADC 134. A ground terminal of second EMI filter 142b may be connected to the floating ground. According to some embodiments, an input terminal of third EMI filter 142c may be configured to receive second sensor 124 measurement data via second line 112b. An output terminal of third EMI filter 142c may be electrically coupled to ADC 134 and may be configured to relay filtered second sensor 124 measurement data to ADC 134. A ground terminal of third EMI filter 142c may be connected to the floating ground.

According to some embodiments, sensor assembly 102 may be powered independently of monitor 104 (e.g. sensor assembly 102 is not powered via monitor 104 but by a battery). In such embodiments, the ground terminals of second EMI filter 142b and third EMI filter 142c may be connected to a second floating ground.

According to some embodiments, second EMI filter 142b and third EMI filter 142c may be positioned in proximity to ADC 134, e.g. on main board 136 of monitor 104 (near or adjacent to ADC 134). According to some embodiments, second EMI filter 142b and third EMI filter 142c may be positioned at respective entrances of ADC 134. According to some embodiments, second EMI filter 142b and third EMI filter 142c may be positioned such that the output terminals thereof are adjacent to ADC 134. According to some embodiments, first EMI filter 142a may be positioned at a distance (indicated by a dashed double-headed arrow D1) of less than about 5 cm, less than about 2 cm, or less than about 1 cm from first sensor 122. Each possibility is a separate embodiment.

According to some embodiments, second EMI filter 142b may be positioned at a distance (indicated by a dashed double-headed arrow D2) of less than about 10 cm, less than about 5 cm, less than about 2 cm, or less than about 1 cm from ADC 134. Each possibility is a separate embodiment.

According to some embodiments, third EMI filter 142c may be positioned at a distance (indicated by a dashed double-headed arrow D3) of less than about 10 cm, less than about 5 cm, less than about 2 cm, or less than about 1 cm from ADC 134. Each possibility is a separate embodiment.

According to some embodiments, ADC 134 may refer to a plurality of ADCs, each communicatively associated with a different sensor. Thus, for example, according to some embodiments, EMI filter 142b may be associated with a first ADC and second EMI filter 142c may be associated with a second ADC.

According to some embodiments, including embodiments wherein sensor assembly 102 is a finger probe, sensor assembly 102 may include a substrate (e.g. a printed circuit board) on which first sensor 122, second sensor 124, and first EMI filter 142a may be mounted/positioned (as well as control circuitry and additional non-electrode-based sensors, such as, but not limited to, an accelerometer and a thermistor, as essentially described herein). According to some embodiments, first sensor 122 may not be positioned on the substrate, but rather be positioned on a separate disposable (replaceable) element (not shown) configured for use with sensor assembly 102. According to some embodiments, first EMI filter 142a may also not be positioned on the substrate but instead on the disposable element. According to some embodiments, the disposable element is configured to be attached to or mounted within sensor assembly 102 such that contact is established between the electrodes of first sensor 122 and the subject's skin. According to some embodiments, the disposable element is flexible and the electrodes of first sensor 122 form an electrode array on the disposable element. According to some embodiments, the disposable element includes an electrical connector, on an end thereof, configured to connect to a matching electrical connector in sensor assembly 102 such as to electrically couple first sensor 122 to the printed circuit board of sensor assembly 102. According to some embodiments, first EMI filter 142a may be positioned between first sensor 122 and the electrical connector.

As a non-limiting example, each of EMI filters 142 may be a low ESL (equivalent series inductance) feed-through capacitor with three terminals (input, output, and ground), as known in the art.

According to some embodiments, first EMI filter 142a is different than the rest of the EMI filters (in particular, second EMI filter 142b and third EMI filter 142c), and the capacitance of first EMI filter 142a is between about 0.01 µF and about 1 µF. According to some embodiments, the capacitance of first EMI filter 142a is about 0.1 µF. According to some embodiments, first EMI filter 142a may be a (no-polarity) chip multilayer ceramic capacitor, such as, for example, from the NFM21 series by Murata.

According to some embodiments, the capacitance of each of second EMI filter 142b and third EMI filter 142c (and EMI filters 142d-142g in embodiments below including additional filters associated with third sensor 162) is between about 1 µF and about 100 µF, between about 20 µF and about 30 µF, or about 27 µF. Each possibility is a separate embodiment. According to some embodiments, each of EMI filters 142b-142g may be a (no-polarity) chip multilayer ceramic capacitor, such as, for example, the NFM31PC276B0J3 EMI filter by Murata.

According to some embodiments, one or more of EMI filters 142 includes at least two serially connected EMI filters, e.g. a low-pass filter and a high-pass filter connected in series.

As used herein, according to some embodiments, electrical lines 112 may include any electrical wires/wirings, conductive tracks (e.g. copper traces when second EMI filter 142b, third EMI filter 142c, and ADC 134 are mounted on main board 136), and the like, which define electrical conduction paths electrically connecting first sensor 122 and second sensor 124 to ADC 134, or to processor 132, without going through ADC 134, when the conveyed signal is digital. For example, in embodiments wherein first sensor 122 is mounted on the disposable element, first line 112a may extend from within the disposable element, via (the control circuitry of) the finger probe, via a cable, and into monitor 104 (e.g. up until ADC 134). According to some embodiments, in between sensor assembly 102 and monitor 104 electrical lines 112 extend along a common cable. According to some embodiments, the cable may be a 2.8 m cable.

According to some embodiments, monitoring system 100 includes one or more amplifiers 152 for amplifying analog sensor data. In particular, data relayed to second EMI filter 142b and third EMI filter 142c may be amplified first to increase the noise-resistance thereof. For example, and as depicted in FIG. 1, according to some embodiments, monitor 104 includes a first amplifier 152a and a second amplifier 152b (of amplifiers 152) configured for amplifying first sensor 122 and second sensor 124 data. First amplifier 152a may be mounted on first line 112a before second EMI filter 142b. Second amplifier 152b may be mounted on second line 112b before third EMI filter 142c.

According to some embodiments, amplifiers 152 are housed within a single unit.

According to some embodiments, and as depicted in FIG. 1, sensor assembly 102 may further include a third (non-electrode-based) sensor 162, such as, but not limited to, an accelerometer (e.g. a digital accelerometer). An accelerometer may be used to measure/detect e.g. movements/shivering/spasms of a subject. According to some embodiments, third sensor 162 may be electrically associated with at least one additional EMI filter positioned in monitor 104. As a non-limiting example, according to some embodiments, including embodiments, wherein third sensor 162 is a digital accelerometer, third sensor 162 may be electrically associated with, for example, three EMI filters, or as depicted in FIG. 1, four EMI filters: a fourth EMI filter 142d, a fifth EMI filter 142e, a sixth EMI filter 142f, and a seventh EMI filter 142g. EMI filters 142d, 142e, 142f, and 142g are electrically associated with third sensor 162 via a third line 112c, a fourth line 112d, a fifth line 112e, and a sixth line 112f, respectively (from electrical lines 112). Filtered third sensor 162 measurement data may be directly conveyed from EMI filters 142d-142g to processor 132 when third sensor 162 output is digital. According to some embodiments, EMI filters 142d-142g are not grounded, for example, in embodiments wherein third sensor 162 is a digital accelerometer, as the high capacitance (e.g. above 10 µF) of EMI filters 142d-142g may lead to communication failure between the accelerometer and processor 132. According to some embodiments, EMI filters 142b-142g may be identical or substantially identical and/or have substantially identical properties.

According to some embodiments, and as depicted in FIG. 1, sensor assembly 102 may further include a fourth (non-electrode-based) sensor 172, such as, but not limited to, a thermometer configured to measure the temperature of a subject. According to some embodiments, fourth sensor 172 is a thermistor. A fourth sensor 172 dedicated line 112g may be configured to relay fourth sensor 172 measurement data to processor 132. According to some embodiments, monitor 104 may include a third amplifier 152c (before processor 132) for amplifying relayed measurement data of fourth sensor 172.

According to some embodiments, when the third or fourth sensor is non-electrode-based and sufficiently electrically insulating, the mounting of EMI filters on the associated electrical lines may be obviated.

Processor 132 may be configured to determine, based on the measurement data received from sensor assembly 102 (e.g. measurement data received from first sensor 122 and second sensor 124 and optionally from additional sensors when present), the physiological status (e.g. autonomic nervous system activity or level of pain) of the subject. According to some embodiments, processor 132 may be configured to allow discounting (i.e. not taking into account) any electrical signal received via first line 112a (or any of electrical lines 112 which is connected to an electrode-based sensor) when assessing (computing) the physiological status of a patient during a diathermy procedure, an RF ablation procedure, and the like. Specifically, processor 132 may be configured to allow discounting any electrical signal picked up by the electrodes of first sensor 122.

According to some embodiments, processor 132 may be configured to detect when a diathermy (or RF ablation) electrical current/voltage is applied to a patient. According to some embodiments, processor 132 may be configured to so detect based on the measurement data received from sensor assembly 102, e.g. based on the level of noise in the measurement data. According to some embodiments, upon detecting the application of a diathermy (or RF ablation) electrical current, processor 132 may discount the measurement data of any of electrical lines 112 which are connected to an electrode-based sensor (e.g. first line 112a) in assessing the physiological status of the patient.

According to some embodiments, processor 132 may be configured to estimate the noise introduced through first sensor 122, and to take into account the noise estimation in the assessing of the physiological status of the patient (during a diathermy procedure, an RF ablation procedure, and the like).

According to some embodiments, sensor assembly 102 and monitor 104 may include electrical switches and electrical bypass elements (not shown) which allow switching between two configurations: A first configuration wherein EMI filters 142 may be decoupled and measurement data may thus not be relayed therethrough, being relayed instead via the electrical bypass elements, and a second configuration wherein EMI filters 142 may be coupled and measurement data may be relayed through EMI filters 142, as described above. According to some embodiments, processor 132 may be configured to switch from the first configuration to the second configuration when application of diathermy (or RF ablation) electrical currents is detected.

According to some embodiments, sensor assembly 102 is configured to allow an operator to select which of the sensors are active (e.g. the operator can choose whether to activate first sensor 122, second sensor 124, or both). According to some embodiments, any electrode-based sensor, such as first sensor 122 may be controllably disabled during a diathermy procedure.

Figure 2:
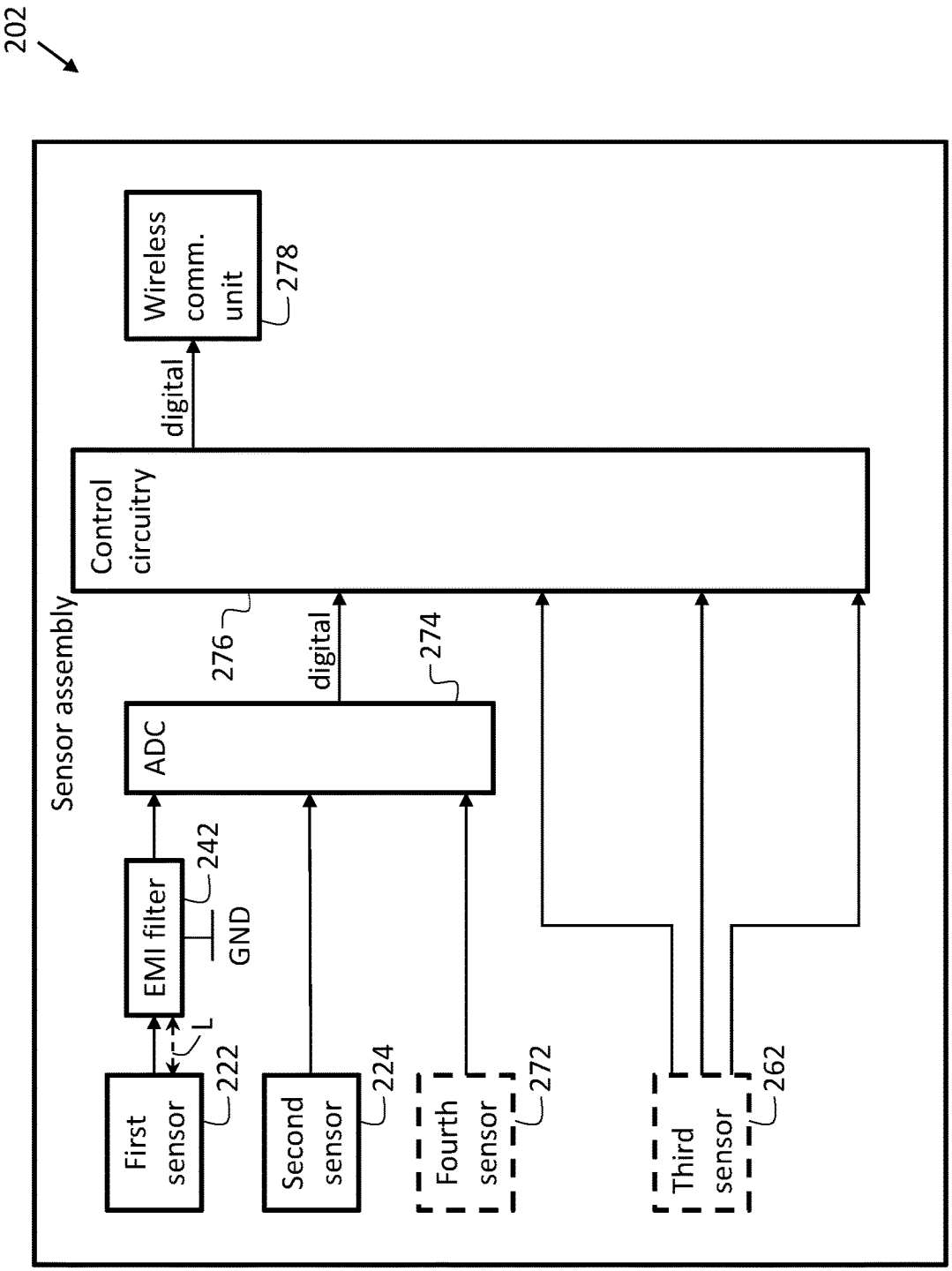
FIG. 2 is a block diagram of a sensor assembly configured for monitoring one or more physiological parameters during an interventional medical procedure, such as a diathermy surgical procedure, according to some embodiments.

Making reference to FIG. 2, according to an aspect of some embodiments, there is provided a sensor assembly 202. Sensor assembly 202 is similar to sensor assembly 102 but differs therefrom at least in that sensor assembly 202 is wireless. That is, sensor assembly 202 is configured for wireless communication with an associated (external) monitor (not shown), which may be configured to process sensor measurement data received from sensor assembly 102, such as to assess a physiological status (e.g. level of pain or nociception) of a patient during a diathermy surgical procedure or an RF ablation procedure.

Additionally or alternatively, according to some embodiments, the processing of the sensor measurement data may be performed by the wireless sensor assembly, and, in particular, the control circuitry, as further elaborated hereinbelow.

According to some embodiments, sensor assembly 202 may be configured to be mounted/placed on a forehead, a back, a chest, a foot, an arm, a hand, and/or an ear (e.g. in the earlobe). Each possibility is a separate embodiment. According to some embodiments, sensor assembly 102 may be a finger probe.

More specifically, sensor assembly 202 includes a first (electrode-based) sensor 222 and a second (non-electrode-based) sensor 224 similar to first sensor 122 and second sensor 124, respectively. Sensor assembly 202 further includes an EMI filter 242, an ADC 274, control circuitry 276 (including e.g. a micro-controller), and a wireless communication unit 278. Control circuitry 276 is functionally associated with sensors 222 and 224, and with wireless communication unit 278 and is configured to control the operation thereof.

EMI filter 242 is similar to first EMI filter 142a. EMI filter 242 is electrically coupled to first sensor 222, such as to filter first sensor 222 measurement data. Filtered first sensor 222 measurement data is conveyed from EMI filter 242 to ADC 274, and therefrom to wireless communication unit 278.

According to some embodiments, an input terminal of EMI filter 242 may be electrically coupled to first sensor 222 and may be configured to receive therefrom measurement data of first sensor 222. An output terminal of EMI filter 242 may be configured to relay first sensor 222 filtered measurement data to ADC 274. A ground terminal of EMI filter 242 may be connected to a ground. According to some embodiments, the ground is a floating ground.

According to some embodiments, EMI filter 242 may be positioned at a distance (indicated by a dashed double-headed arrow L) of less than about 5 cm, less than about 2 cm, or less than about 1 cm from first sensor 222. Each possibility is a separate embodiment.

As a non-limiting example, EMI filter 242 may be a low ESL feed-through capacitor with three terminals (input, output, and ground), as known in the art. According to some embodiments, the capacitance of the capacitor is between about 0.01 µF and about 1 µF. According to some embodiments, the capacitance of the capacitor is about 0.1 µF. According to some embodiments, the capacitor may be a (no-polarity) chip multilayer ceramic capacitor, such as, for example, from the NFM21 series by Murata.

According to some embodiments, EMI filter 242 may be mounted adjacently to/near first sensor 222, and ADC 274 may optionally be mounted adjacently to/near EMI filter 242, such as to minimize the length of electrical lines (not numbered) connecting/coupling EMI filter 242 to first sensor 222 and ADC 274. As used herein, according to some embodiments, "electrical lines" may include any type of electrical conduction paths (e.g. conductive tracks on a PCB), or electrical connections, directly or indirectly (e.g. when an EMI filter is mounted on the line) electrically coupling first sensor 222 and second sensor 224 to ADC 274, or to control circuitry 272, without going through ADC 274, when the conveyed signal is digital.

According to some embodiments, wherein second sensor 224 output is analog, second sensor 224 is configured to relay measurement data thereof to ADC 274, wherefrom the measurement data is relayed to control circuitry 276 which further relays the measurement data to wireless communication unit 278. According to some embodiments, wherein second sensor 224 output is digital, second sensor 224 measurement data is relayed to wireless communication unit 278 (via control circuitry 276) without passing through ADC 274.

According to some embodiments, one or more of the non-electrode-based sensors may be optically coupled to the control circuitry, e.g. via an optical fiber.

According to some embodiments, sensor assembly 202 further includes one or more additional (non-electrode-based) sensors: a third sensor 262 and/or a fourth sensor 272 similar to third sensor 162 (e.g. an accelerometer) and fourth sensor 172 (e.g. a thermometer). According to some embodiments, wherein the output of third sensor 272 is digital, such as embodiments wherein third sensor 272 is a digital accelerometer, third sensor 272 may be communicatively associated with control circuitry 276 via a plurality of electrical lines (not numbered), for example, three lines (as depicted in FIG. 2) or four lines.

Wireless communication unit 278 is configured to send to the associated monitor measurement data obtained by the sensors.

According to some embodiments, sensor assembly 202 may include amplifiers (not shown) mounted between the sensors and ADC 274, such as to amplify respective sensor signals. More specifically, an amplifier associated with first sensor 222 may be mounted between EMI filter 242 and ADC 274, such as to amplify a filtered first sensor 222 signal.

According to an aspect of some embodiments, not depicted in the figures, there is provided a monitoring system including a plurality of physiological sensors. The monitoring system is similar to sensor assembly 202 but differs therefrom in that the monitoring system constitutes a single unit of which both the plurality of sensors and the monitor are integral parts (unlike the case with sensor assembly which is associated with an external monitor). More specifically, the components of the monitoring system may be housed within a single unit (housing) with the processing of the sensor readings being performed within the unit. In particular, the unit includes processing circuitry (which may be similar to the processing circuitry in monitor 104) configured to assess the physiological status of a patient based on the sensor readings. The unit may further include a user interface, which may include a display. It is noted that the sensors, an EMI filter, and an ADC of the monitoring system may be arranged similarly to sensors 222 and 224 (and sensors 262 and 272 in embodiments including a third and a fourth sensor), EMI filter 242, and ADC 274.

The skilled person will understand that while some of the discussion regarding monitoring system 100/sensor assembly 202 has focused on embodiments configured for assessing the level of pain experienced by a patient during a diathermy surgical procedure, the scope of the application also covers embodiments wherein monitoring system 100/sensor assembly 202 is additionally or alternatively configured for assessing a degree/level of anesthesia, nociception, sleep, stress, anxiety, and/or analgesia of a subject during a diathermy surgical procedure. More generally, the scope of the application also covers embodiments wherein monitoring system 100/sensor assembly 202 is configured for gauging an autonomic nervous system activity of a subject during a diathermy surgical procedure. Even more generally, the scope of the application also covers embodiments wherein monitoring system 100/sensor assembly 202 is configured for reliably monitoring at least one physiological parameter using a non-electrode-based sensor of a subject during a diathermy surgical procedure in the presence of an electrode-based sensor mounted on the subject's body and electromagnetically interfering with readings/signals of the non-electrode-based sensor (e.g. due to the non-electrode-based sensor the electrode-based sensor being positioned in proximity to one another).

The skilled person will also understand that while some of the discussion regarding monitoring system 100/sensor assembly 202 has focused on embodiments wherein sensor assembly 102/sensor assembly 202 is a finger probe, the scope of the application covers any multi-sensor assembly/probe, including or associated with an electrode-based sensor (e.g. first sensor 122 or similar thereto), configured to close an electrical conduction path in a body of a subject, and at least one non-electrode-based sensor (e.g. second sensor 124 or similar thereto). In particular, sensor assembly 102/sensor assembly 202 may be configured to be mounted/placed on a forehead, a back, a chest, a foot, a hand (additionally or alternatively on locations other than a finger), and/or an ear.

Finally, the skilled person will understand that while some of the discussion regarding monitoring system 100/sensor assembly 202 has focused on diathermy, monitoring system 100 may also be used for reliably assessing a patient's physiological status (e.g. autonomic nervous system activity) during an RF ablation procedure, and, more generally, for reliably monitoring physiological parameters during an RF ablation procedure. In fact, RF ablation procedures are typically characterized by operating frequencies (i.e. the frequency of the applied AC current/voltage) in the range of 350 kHz to 500 kHz overlapping with the operating frequencies of diathermy surgical equipment, thereby rendering the disclosed EMI filters (e.g. EMI filters 142) suitable also for suppressing RF ablation-induced noise. More generally, the skilled person will understand that monitoring system 100/sensor assembly 202 may be used for reliably assessing a patient's physiological status during any procedure involving application of high intensity/energy radiofrequency electrical currents/voltages through a body of a patient.

As used herein, according to some embodiments, the terms "sensor data" (and corresponding derivatives such as "sensing data") and "measurement data" are interchangeable. According to some embodiments, the terms "sampling" and "measurement" (and corresponding derivatives such as "to sample" and "to measure") are interchangeable.

As used herein, according to some embodiments, the terms "subject" and "patient" are interchangeable.

As used herein, according to some embodiments, the terms "first EMI filter" and "proximal EMI filter" may be interchangeable. According to some embodiments, the terms "second EMI filter" and "distal EMI filter" may be interchangeable.

As used herein, according to some embodiments, the terms "sensor data", with reference to measurement data of the sensor transmitted/relayed/sent via an electrical line, is interchangeable with "sensor signal(s)".

As used herein, according to some embodiments, the term "coupling" (and derivatives thereof such as "coupled"), with reference to two electrically associated elements/components, may refer to "direct" coupling, wherein the two elements are directly connected by an electrical line, as well as to "indirect" coupling, wherein a third element, such as an amplifier, is present on the electrical line in between the two elements.

As used herein, according to some embodiments, the term "proximal" with reference to positioning of elements/components, may refer to elements/components located on or near the body of a subject (e.g. in the finger probe worn by the subject). According to some embodiments, the term "distal" with reference to positioning of elements/components, may refer to elements/components which are not located near to the body of a subject (e.g. on the monitor).

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. No feature described in the context of an embodiment is to be considered an essential feature of that embodiment, unless explicitly specified as such.

Although steps of methods according to some embodiments may be described in a specific sequence, methods of the disclosure may include some or all of the described steps carried out in a different order. A method of the disclosure may include a few of the steps described or all of the steps described. No particular step in a disclosed method is to be considered an essential step of that method, unless explicitly specified as such.

Although the disclosure is described in conjunction with specific embodiments thereof, it is evident that numerous alternatives, modifications and variations that are apparent to those skilled in the art may exist. Accordingly, the disclosure embraces all such alternatives, modifications and variations that fall within the scope of the appended claims. It is to be understood that the disclosure is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the disclosure. Section headings are used herein to ease understanding of the specification and should not be construed as necessarily limiting.

What is claimed is:

1. A system comprising:
   a sensor assembly configured to monitor a physiological status of a subject, which comprises:
   an electrode-based sensor, which is configured to close an electrical conduction path passing through a body of the subject, and
   at least one non-electrode-based sensor configured to monitor one or more physiological parameters of the subject during a medical interventional procedure involving an application of at least one chosen from:
   1. high intensity radiofrequency electrical currents,
   2. high intensity radiofrequency electrical voltages,
   3. high energy radiofrequency electrical currents, and
   4. high energy radiofrequency electrical voltages; and
   a first electromagnetic interference (EMI) filter coupled to the electrode-based sensor and configured to suppress noise in a signal of the non-electrode-based sensor, the noise being induced, via the electrode-based sensor, by medical interventional equipment during the medical interventional procedure; and further comprising a plurality of electrical lines, a second EMI filter, a third EMI filter, an ADC, and a monitor, which comprises a processor;
   wherein the plurality of electrical lines electrically associates the sensor assembly with the monitor, the plurality of electrical lines comprising:
   a first line configured to transmit signals from electrode-based sensor to the monitor; and
   a second line configured to transmit signals from the non-electrode-based sensor to the monitor;
   wherein the first EMI filter and second EMI filter are mounted on the first line, the first EMI filter being positioned between the electrode-based sensor and the second EMI filter, and wherein the third EMI filter is mounted on the second line;
   wherein the noise suppression of the signal of the non-electrode-based sensor is effected by attenuating frequencies in a first frequency range by 10 dB, or more, as compared to frequencies in a second frequency range, the first frequency range comprising the radiofrequency of the applied electrical currents or voltages, and the second frequency range comprising a sampling frequency of the sensor assembly;
   wherein each of the second EMI filter and the third EMI filter is characterized by a respective frequency response curve with a magnitude of an attenuation in the first frequency range being greater by at least 10 dB than a magnitude of an attenuation in the second frequency range; and
   wherein the processor is configured to assess the physiological status of a subject based at least on the signals of the non-electrode-based sensor.

2. The system of claim 1, wherein the magnitude of the attenuation of the second and/or the third EMI filters in the first frequency range is at least 60 dB.

3. The system of claim 1, wherein the non-electrode-based sensor is, or comprises, a PPG sensor, the first line extends from the electrode-based sensor to the ADC, and the second line extends from the non-electrode-based sensor to the ADC;
   wherein an input terminal of the first EMI filter is coupled to the electrode-based sensor, wherein an output terminal of the first EMI filter is configured to transmit, via the first line, signals, induced in the electrode-based sensor during the medical interventional procedure and filtered by the first EMI filter, and wherein a ground terminal of the first EMI filter is connected to a floating ground;
   wherein an input terminal of the second EMI filter is configured to receive, via the first line, signals from the first EMI filter, wherein an output terminal of the second EMI filter is coupled to the ADC, and wherein a ground terminal of the second EMI filter is connected to the floating ground; and
   wherein an input terminal of the third filter is configured to receive, via the second line, the signals of the non-electrode-based sensor, an output terminal of the third filter is coupled to the ADC, and a ground terminal of the third filter is connected to the floating ground.

4. The system of claim 3, further comprising a first amplifier and a second amplifier, wherein the first amplifier is mounted on the first line between the first EMI filter and second EMI filter, the first amplifier being configured to amplify the signals transmitted by the first EMI filter; and wherein the second amplifier is mounted on the second line proximally to the third EMI filter, the second amplifier being configured to amplify the signals received from the non-electrode-based sensor.

5. The system of claim 3, wherein the first EMI filter is housed within the sensor assembly near or adjacently to the electrode-based sensor, wherein the ADC, the second EMI filter, the third EMI filter, the first amplifier, and the second amplifier are housed within the monitor, and wherein each of the second EMI filter and the third EMI filter is positioned near or adjacently to the ADC.

6. The system of claim 3, wherein each of the EMI filters is a low ESL (equivalent series inductance) feed-through capacitor, wherein a capacitance of the first EMI filter is between 0.05 µF and 0.2 µF, and wherein capacitances of the second EMI filter and the third EMI filter are between 15 µF and 40 µF.

7. The system of claim 1, wherein the assessing of the physiological status comprises discounting data received from the electrode-based sensor and/or cleaning the signals obtained from the non-electrode-based sensor based on an estimation of the noise induced, via electrode-based sensor, by the medical interventional equipment.

8. The system of claim 1, wherein the non-electrode-based sensor comprises a PPG sensor;

wherein the sensor assembly further comprises a digital accelerometer, wherein the system further comprises at least three additional lines and at least three additional EMI filters, each of the at least three additional EMI filters being mounted on a respective line from at the least three additional lines, and wherein the additional lines are configured to relay signals of the accelerometer, via the EMI filters, to the processor; and, optionally, wherein the sensor assembly further comprises a thermometer, wherein the system further comprises a thermometer-dedicated line and an amplifier mounted on the thermometer-dedicated line, and wherein the thermometer-dedicated line is configured to relay signals of the thermometer, via the said amplifier, to the ADC.

9. The system of claim 1, wherein, in between the sensor assembly and the monitor, the plurality of electrical lines is housed within an electrical cable.

* * * * *